United States Patent [19]

Cliffe et al.

[11] Patent Number: 5,693,642

[45] Date of Patent: Dec. 2, 1997

[54] PIPERAZINE DERIVATIVES AS 5-HT$_{1A}$ LIGANDS

[75] Inventors: Ian Anthony Cliffe; Mark Antony Ashwell, both of Slough; Terence James Ward, Reading; Alan Chapman White, Staines; Graham John Warrellow, Northwood, all of England

[73] Assignee: John Wyeth & Brother Ltd., United Kingdom

[21] Appl. No.: 436,411

[22] PCT Filed: Mar. 17, 1994

[86] PCT No.: PCT/GB94/00539

§ 371 Date: May 24, 1995

§ 102(e) Date: May 24, 1995

[87] PCT Pub. No.: WO94/21610

PCT Pub. Date: Sep. 29, 1994

[30] Foreign Application Priority Data

Mar. 24, 1993 [GB] United Kingdom ............... 9306103

[51] Int. Cl.$^6$ .................. A61K 31/495; A61K 31/505; C07D 401/06; C07D 401/14

[52] U.S. Cl. .................. 514/252; 514/254; 544/295; 544/360; 544/363; 544/364

[58] Field of Search .................... 544/360, 295, 544/363, 364; 514/252, 254

[56] References Cited

U.S. PATENT DOCUMENTS 5,346,896 9/1994 Ward et al. ..................... 544/394

FOREIGN PATENT DOCUMENTS

| | | |
|---|---|---|
| 0512755 | 11/1992 | European Pat. Off. |
| 2248449 | 4/1992 | United Kingdom. |
| 9206082 | 4/1992 | WIPO. |

OTHER PUBLICATIONS

H. Morren et al., Industrie Chimique Belge, 1963, 28, 123–134.

*Primary Examiner*—Emily Bernhardt
*Attorney, Agent, or Firm*—R. F. Boswell, Jr.

[57] ABSTRACT

Piperazine derivatives of formula (I) and their salts are 5-HT$_{1A}$ binding agents and may be used, for example, as anxiolytics. In the formula, R, R$^2$ and R$^4$ are hydrogen or lower alkyl, R$^1$ is mono- or bicyclic aryl or heteroaryl, R$^3$ is lower alkyl or cycloalkyl, A is an alkylene chain and X is —CO—, —CR$^5$OH— (where R$^5$ is hydrogen, lower alkyl or cycloalkyl), —S—, —SO— or —SO$_2$— or X can also be —(CH$_2$)$_n$— (where n is 0, 1 or 2) when R$^3$ is cycloalkyl.

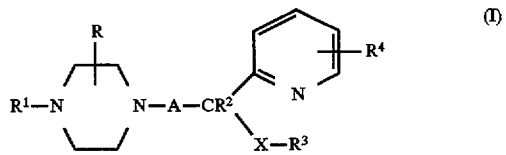

6 Claims, No Drawings

PIPERAZINE DERIVATIVES AS 5-HT$_{1A}$ LIGANDS

This application is a 371 of PCT/GB 94/00539 filed Mar. 17, 1994.

This invention relates to piperazine derivatives, to processes for their preparation, to their use and to pharmaceutical compositions containing them. The novel compounds act upon the central nervous system by binding to 5-HT receptors (as more fully explained below) and hence can be used as medicaments for treating human and other mammals.

The novel compounds of the invention are those of the general formula

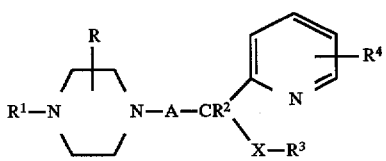
(I)

and the pharmaceutically acceptable acid addition salts thereof.

In formula (I):

R represents hydrogen or one or two same or different (lower)alkyl groups $R^1$ is a mono- or bicyclic aryl or heteroaryl radical $R^2$ is hydrogen or lower alkyl $R^3$ is lower alkyl or cycloalkyl $R^4$ is hydrogen or lower alkyl A is an alkylene chain of 1 to 3 carbon atoms optionally substituted by one or more lower alkyl groups and X is —CO—. —CR$^5$OH— (where R$^5$ is hydrogen, lower alkyl or cycloalkyl) —S—, —SO— or —SO$_2$— or X can also be —(CH$_2$)$_n$— (where n is 0, 1 or 2) when R$^3$ is cycloalkyl.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl. A cycloalkyl group preferably contains 3 to 7 carbon atoms. Examples of the cycloalkyl group R$^3$ include cyclopropyl, cyclobutyl, cyclopentyl, cyclohexyl and cycloheptyl.

When used herein "aryl" means an aromatic radical having 6 to 12 carbon atoms (eg phenyl or naphthyl) which optionally may be substituted by one or more substituents. Preferred substituents are lower alkyl, lower alkoxy (eg methoxy, ethoxy, propoxy, butoxy), halogen, halo(lower) alkyl (eg trifluoromethyl), nitro, nitrile, amido, (lower) alkoxycarbonyl, amino, (lower)alkylamino or di(lower) alkylamino substituents. Two substituents on the aromatic ring may be connected together to form another ring system. For example R$^1$ may be a bicyclic oxygen-containing radical of the formula

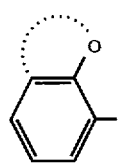

wherein the heterocyclic ring containing the oxygen atom contains a total of 5 to 7 ring members, said heterocyclic ring being saturated or unsaturated and optionally containing one or more hetero ring members (eg O, N or S) in addition to the oxygen atom illustrated and the bicyclic oxygen radical being optionally substituted by one or more substituents such as the substituents mentioned above in connection with "aryl". A preferred example of such a bicyclic oxygen radical is an optionally substituted radical of the formula

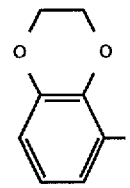

Preferably R$^1$ is a phenyl radical containing a substituent in the ortho position. A particularly preferred example of R$^1$ is o-(lower)alkoxyphenyl eg o-methoxyphenyl.

The term "heteroaryl" refers to an aromatic radical containing one or more hetero ring atoms (eg oxygen, nitrogen, sulphur) and which may be optionally substituted by one or more substituents. Examples of suitable substituents are given above in connection with "aryl" radicals. The heteroaryl radical may, for example, contain up to 10 ring atoms. Preferably the heteroaryl radical is a monocyclic radical containing 5 to 7 ring atoms. Preferably the hetero ring contains a nitrogen hetero atom with or without one or more further hetero atoms. When R$^1$ is a heteroaryl group it is preferably an optionally substituted pyrimidyl, quinolinyl, isoquinolinyl, or indolyl radical.

Preferred compounds have the following substituents either independently or in combination:

(a) R is hydrogen (b) R$^1$ is aryl, for example o-(lower)alkoxyphenyl (eg o-methoxyphenyl) or bicyclic heteroaryl (eg indolyl)

(c) R$^2$ is hydrogen (d) R$^3$ is cycloalkyl, particularly cyclohexyl (e) A is —CH$_2$— or —CH$_2$CH$_2$—

(f) X is —CO—, —CHOH—, —S—, —SO$_2$— or —CH$_2$—.

The compounds of the invention may be prepared by methods known in the art from known starting materials or starting materials that may be prepared by conventional methods.

One method of preparing the compounds of the invention comprises alkylating a piperazine derivative of formula

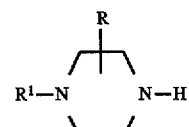
(II)

with an alkylating agent providing the group

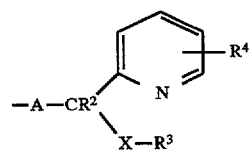
(III)

The alkylating agent may be, for example, a compound of formula

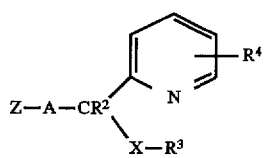
(IV)

where $R^2$, $R^3$, $R^4$, X and A are as defined above and Z is a leaving group such as halogen or an alkyl- or arylsulphonyloxy group.

The compounds of formula (I) in which X is —CHOH—, —S— or —CH$_2$— may also be prepared by reduction of an amide of formula

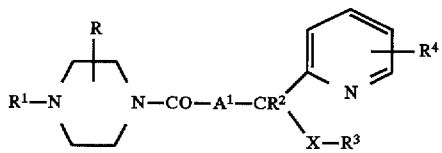
(V)

where R, $R^1$, $R^2$, $R^3$, and $R^4$ are as defined above and X is —CHOH—, —S— or —CH$_2$— and $A^1$ is an alkylene radical of 1 or 2 carbon atoms optionally substituted by one or more (lower)alkyl groups. The reduction may, for example, be carried out with a hydride transfer agent e.g. borane-dimethylsulphide or lithium aluminium hydride. The starting amide of formula (V) may be made by acylating a piperazine derivative of formula (II) above with an acylating derivative of an acid or formula

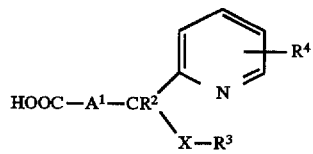
(VI)

The acylating derivative may be, for example, the acid chloride.

Another method of preparing the compounds of the invention wherein X is —CR$^5$OH—, —CH$_2$— or a single bond comprises reacting a compound having the anion

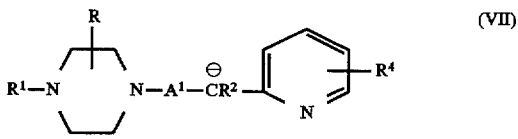
(VII)

with a compound of formula

R$^3$R$^5$CO    (VIIIa)

or

R$^3$(CH$_2$)$_m$Y    (VIIIb)

where $R^2$ and $R^3$ are as defined above, m is 0 or 1 and Y is a leaving group such as halogen. Reaction of the aldehyde or ketone (VIIIa) with the anion gives a compound of the invention in which X is CR$^5$OH while reaction of the compound (VIIIb) with the anion gives a compound of the invention in which X is CH$_2$ or a single bond. The anion (VII) may be prepared by known methods. For example the anion may be prepared by reacting the compound

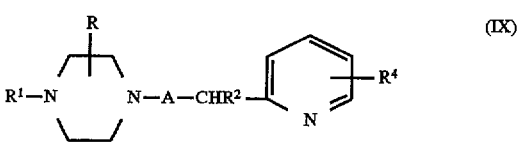
(IX)

with a base e.g. n-butyl lithium.

Compounds of the invention in which X is —CO— may be prepared by oxidation of compounds in which X is —CHOH— and compounds of the invention in which X is —CHOH— or —CH$_2$— may be prepared by reduction of compounds in which X is —CO—.

Compounds of the invention in which X is S may be prepared by reacting the anion (VII) as defined above with a compound of formula $R^3$—S—S—$R^3$ (eg isopropyldisulphide or cyclohexyldisulphide). Compounds of the invention in which X is S may be oxidised to compounds of the invention in which S is SO or SO$_2$. The oxidation may be carried out with a peroxidising agent (eg hydrogen peroxide).

If in any of the other processes mentioned herein, a substituent on the group R 1 is other than the one required the substituent may be convened to the desired substituent by known methods.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain an asymmetric carbon atom, so that the compounds can exist in different steroisomeric forms. The compounds can be for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. In pharmacological testing it has been shown that the compounds particularly bind to receptors of the 5-HT$_{1A}$ type. In general, the compounds selectively bind to receptors of the 5-HT$_{1A}$ type to a much greater extent than they bind to other receptors such as $\alpha_1$ and $D_2$ receptors. Many exhibit activity as 5-HT$_{1A}$ antagonists in pharmacological testing. The Compounds of the invention can be used for the treatment of CNS disorders, such as anxiety in mammals, particularly humans. They may also be used as antidepressants, antipsychotics, hypotensives and as agents for regulating the sleep/wake cycle, feeding behaviour and/or sexual function and as cognition enhancing agents.

The compounds of the invention were tested for 5-HT$_{1A}$ receptor binding activity in rat hippocampal membrane homogenate by the method of B. S. Alexander and M. D. Wood, J Pharm Pharmacol, 1988, 40, 888–891. The results for representative compounds of the invention are as follows:

| Compound | IC$_{50}$(nM) |
| --- | --- |
| Example 1a | 4 |
| Example 1b | 4.3 |
| Example 2a | 2.0 |
| Example 2b | 1.8 |
| Example 3 | 2.6 |
| Example 4 | 1.6 |
| Example 5 | 40 |
| Example 6 | 4.25 |
| Example 7 | 15 |

The compounds are tested for 5-HT$_{1A}$ receptor antagonism activity in a test involving the antagonism of 5-carboxamidotryptamine in the guinea-pig ileum in vitro (based upon the procedure of Fozard et al, Br J Pharmac, 1985, 86, 601P).

The invention also provides a pharmaceutical composition comprising a compound of formula I or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents. lubricants. solubilisers. suspending agents, fillers, glidants, compression aides, binders or tablet-disintegrating agents; it can also be an encapsulating material. In powders the carrier is a finely divided solid which is in admixture with the finely divided active ingredient.

In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The ten "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution, alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compostions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

(a) R*, R*-1-(2Methoxyphenyl)-4-[(2-propan-(2-pyridinyl)-3-cyclohexyl)-3-ol]piperazine and (b) R*, S*-1-(2-Methoxyphenyl)-4-[(2-propan-(2-pyridinyl)-3-cyclohexyl)-3-ol]piperazine To a solution of 1-(2-methoxyphenyl)-4-(2-pyridinylethyl)piperazine (8.11 g, 27.3 mmol) in THF (anhydrous, 50 ml) at −78° C. under argon was added with stirring n-BuLi (23.8 ml, 1.26M).The addition was at such a rate as to maintain an internal temperature of −75° C. or below. The solution was stirred at −78° C. for 15 minutes. The aldehyde, 1-formylcyclohexane, (3.36 g, 30 mmol) in THF (10 ml) was added dropwise. Water (1 ml) in THF 5 ml) was added in one portion after five minutes and the solution allowed to warm to room temperature. The solvent was removed and the residue dissolved in chloroform (30 ml). The products were removed by washing with HCl (1N, 500 ml). The acidic extract was washed with ether and then adjusted to pH 12 by the addition of solid sodium hydroxide and cooling. The basic solution was extracted with chloroform, washed with saturated salt solution, dried (MgSO$_4$) filtered and reduced to a viscous oil (11.0 g).

The diastereomeric alcohols were separated by silica gel column chromatography using ether as eluant. The least polar component was the title compound (a) and the hydrochloride was obtained by dissolving in chloroform and adding ethereal HCl. Recrystallisation from methanol and ether gave the title compound (a) hydrochloride, m.p. 155°–156° C.

$C_{25}H_{35}N_3O_2.2.5HCl.2H_2O$ requires: C, 55.94; H, 7.79; N, 7.83%. Found: C, 56.14; H, 7.58; N, 7.71%.

The more polar component was the title compound 1(b) and this was converted to the hydrochloride. Crystallisation from methanol/ether gave the title compound (b) hydrochloride, m.p. 135°–136° C.

$C_{25}H_{35}N_3O_2.3HCl.H_2O$ requires: C. 55.92: H. 7.51: N. 7.83% Found: C. 55.64: H. 7.45: N. 7.71%.

EXAMPLE 2

(a) R*,R*-1-(2-Methoxyphenyl)-4-[3-butan-(2-pyridinyl)-4-cyclohexyl)-4-ol]piperazine and (b) R*,S*-1-(2-Methoxyphenyl)-4-[3-butan-(2-pyridinyl)-4-cyclohexyl)-4-ol]piperazine To a cooled (−78° C. internal) solution of 1-(2-methoxyphenyl)-4-(3-pyridinylpropyl)piperazine (2.15 g, 6.63 mol) under argon in THF (15 ml) was added with stirring n-BuLi (5.78 ml, 1.26M) at such a rate that the temperature did not rise above −60° C. (internal). The solution of the anion was stirred at −78° C. for fifteen minutes. The aldehyde, 1-formylcyclohexane, (0.803 ml, 6.63 mol) in THF (2 ml) was added. After approximately fifteen minutes water was added and the reaction allowed to come to room temperature.

The solvents were removed and the residue portioned between chloroform and water. The organic layer was washed with sat. salt solution, dried ($MgSO_4$) and reduced to a viscous oil following filtration. The residue was purified by silica gel column chromatography under pressure eluting with ether. The two diastereomeric products were separated by repeated column chromatography to yield samples of the two title compounds.

The least polar diastereomer was converted to its hydrochloride salt giving the title compound (a) hydrochloride, m.p. 128°–129° C.

$C_{26}H_{37}N_3O_2.2HCl.1.1.75H_2O$ requires: C, 59.14; H, 8.11; N, 7.96%. Found: C, 59.14; H, 7.91; N, 7.84%.

The more polar diastereomer was convened to its hydrochloride gave the title compound (b) hydrochloride, m.p. 108°–109° C.

$C_{26}H_{37}N_3O_2.2HCl.2.25H_2O$ requires: C. 58.15: H. 8.16: N. 7.82%. Found: C. 58.26: H. 7.75: N. 7.78%.

EXAMPLE 3

1-(2-methoxyphenyl-4-[3-(2-pyridinyl)-4-(cyclohexyl-4- one) butyl]piperazine

The diastereomeric mix of 1-(2-methoxyphenyl)4-[3-butan-(2-pyridinyl)4-cyclohexyl)4-ol]piperazine from Example 2 (1.23 g, 2.91 mmol) was dissolved in dry dichloromethane (5 ml). This was added to a preformed solution of oxalyl chloride (292 ml, 3.35 mmol) and dimethyl sulphoxide (539 ml, 7 mmol) in dichloromethane (dry 75 ml) at −60° C. (internal), over 2 minutes. Following the addition the reaction mixture was stirred at between −50° and −6° C. for fifteen minutes. Triethylamine (2 ml, 14.5 mmol) was added and the reaction allowed to reach 0° C. Dichloromethane (50 ml) was added and the reaction mixture was washed with water and brine and then dried ($MgSO_4$). The organic solvent was removed in vacuo to give an oil. The residue was purified by pressure silica gel column chromatography using ether as eluant. The oil (1.0 g) was dissolved in chloroform and ethereal HCl added to give the title compound as the hydrochloride, m.p. 102°–104° C.

$C_{26}H_{35}N_3O_2.3HCl.1.75H_2O$ requires: C, 55.52; H, 7.44; N, 7.47%. Found: C, 55.57; H, 6.93; N, 7.31%.

EXAMPLE 4

1-(2-Methoxyphenyl)-4-[(4-(cyclohexyl)-3-(2-pyridinyl)butyl]piperazine

To a solution of 1-(2-methoxyphenyl)4-(3-pyridinylpropyl)piperazine (1.0 g, 3.1 mmol) at 0° C. in dry toluene (10 ml) was added n-BuLi (3.9 ml). After a further 10 minutes at 0° C. the suspension was treated with cyclohexylmethyl bromide (0.649 ml, 4.7 mmol). The reaction was allowed to stir at 0° C. for a further 2 hours.

The product was extracted into 1N HCl. The aqueous layer was separated, washed with ether and basified (solid NaOH). The basic aqueous suspension was washed with chloroform (2×70 ml). The organic layer was washed with salt solution, dried ($MgSO_4$) and filtered. Removal of the solvent gave a yellow oil which was purified by pressure silica gel column chromatography using ether as eluant (690 mg). The material was subjected to further chromatography using hexane/ether (1:2) as eluant to give the title compound.

The HCl salt, m.p. 110°–111° C. was prepared by dissolving the free base in chloroform and adding ethereal HCl.

$C_{26}H_{37}N_3O.2HCl.1.25H_2O$ requires: C, 62.08; H, 8.32; N, 8.35%. Found: C, 62.34; H, 8.21; N, 8.23%.

EXAMPLE 5

1-(2-Methoxyphenyl)-4-[1-((1-methyl)thioethyl)-1-(2-pyridinyl)ethyl]piperazine 1-(2-Methhoxyphenyl)-4-[1-(2-pyridinyl)ethyl]piperazine (2.974 g, 10 mmol) was dissolved in anhydrous THF (25 ml) and the solution cooled to −70° C., n-butyllithium (1.6M solution, 7 ml, 11 mmol) was added dropwise. After 10 mins, isopropyl disulphide (1.50 g, 10 mmol) in THF (5 ml) was added and the reaction mixture allowed to warm to room temperature over 2 h. The mixture was poured into water (100 ml), extracted with dichloromethane (3×100 ml), washed with brine (100 ml), dried ($Na_2SO_4$), and concentrated in vacuo. The residue was filtered through a plug of silica to give a colourless oil which was dissolved in ether and treated with ethanolic hydrogen chloride to afford the title compound as trihydrochloride 0.25 hydrate (0.54 g), m.p. 127°–131° C.

(Found: C,51.9; H, 6.9; N, 8.8. $C_{21}H_{29}N_3OS.3HCl.0.25HCl.0.25H_2O$ requires C, 52.0; H, 6.75; N, 8.7%).

EXAMPLE 6

1-(2-Methoxyphenyl)-4-[3-(cyclohexylthio)-3-(2-pyridinyl)propyl]piperazine

To a solution of 1-(2-methoxyphenyl)-4-(3-pyridylpropyl)piperazine (5.13 g, 0.0158 mol) in dry toluene (50 ml) under argon, at an internal temperature of −13° C. was added nBuLi (15.81 ml, 17.39 mmol). The temperature was maintained below −3° C.

After stirring and warming to 0° C. cyclohexyldisulphide (4.0 g. 17.37 mmol) was added over 15 minutes.

The solution was stirred at room temperature for 2 hours. Water was added followed by HCl (1N). The volatiles were removed and the aqueous acid layer washed with ethyl acetate. The acid layer was basified with sodium hydroxide (solid) with cooling and the layer extracted with ethyl acetate several times.

The organic layer thus obtained was washed with saturated NaCl followed by drying with $MgSO_4$. After filtration the solvent was removed and the residue purified by silica gel pressure column chromatography eluting with chloroform/methanol (20/1).

The title compound was obtained (3.6 g) and convened to dihydrochloride dihydrate (m.p. 113°–15° C.).

$C_{25}H_{35}N_3OS.2HCl.2H_2O$ requires C, 56.17; H, 7.73; N, 7.82%. Found: C, 55.99; H, 7.98; N, 7.58%.

EXAMPLE 7

1-(2-Methoxyphenyl)-4-[3-(cyclohexylsulphoxy)-3-(2-pyridinyl)propyl]piperazine To a solution of the sulphide from Example 6 (2.16 g, 5.08 mmol) in acetic acid (15 ml) at room temperature under argon was added with stirring $H_2O_2$ (1.51 ml, 27.5%).

After 6 hours at room temperature a further 0.2 ml of $H_2O_2$ was added and the solution placed in the refrigerator for 48 hours.

The solvent was removed and the residue poured into sodium bicarbonate solution. The product was extracted with dichloromethane, washed with NaCl solution, dried ($MgSO_4$) and filtered. Removal of the solvent gave a yellow oil which was purified under pressure by elution of a silica gel column with chloroform/methanol (50/1). Of the two diastereomeric products thus obtained the least polar material was recolumned to give the title product (300 mg). The HCl salt, m.p. 130°–132° C. was prepared by dissolving the sulphoxide in chloroform and adding ethereal HCl.

$C_{25}H_{35}N_3O_2S.3HCl.2.75H_2O$ requires C, 50.00; H, 7.30: N, 7.00%. Found C. 49.91: H. 7.58: N. 7.07%.

EXAMPLE 8

1-(2-Methoxyphenyl)-4-[3-(cyclohexylsulphonyl)-3-(2-pyridinyl)propyl]piperazine To a stirred solution of 1-(2-methoxyphenyl)-4-[3-(cyclohexylthio)-3-(2-pyridinyl)propyl]piperazine at room temperature was added N-methylmorpholine N-oxide (0.351 g, 3 mmol) followed by a solution of osmium tetroxide in t-butanol (2.5% wt, 630 ml). After eighteen hours sodium metabisulphite (sat.) was added and the reaction mixture stirred vigorously.

The organic material was extracted into chloroform, washed with brine, dried ($MgSO_4$) and filtered. Following removal of the solvent the oil was purified by pressure silica gel column chromatography eluting with a gradient of chloroform/methanol 50/1 20/1/.

The product (340 mg) was dissolved in chloroform/ether and ethereal HCl added. The title compound was obtained as the hydrochloride, an off-white solid, m.p. 135°–137° C.

$C_{25}H_{35}N_3O_3S.2HCl.1.75H_2O$ requires: C, 53.42; H, 7.26; N, 7.48%. Found C, 53.42; H, 7.15; N, 7.46%.

EXAMPLE 9

1-(2-Methoxyphenyl)-4-[5-(cyclohexyl)-3-(2-pyridinyl)pentyl]piperazine

The title compound was prepared following the procedure of Example 4 using cyclohexylethyl bromide as reactant in place of cyclohexylmethyl bromide. The product was obtained as the hydrochloride, m.p. 134°–135° C.

$C_{27}H_{39}N_3O.3HCl.0.5CH_3OH$ requires: C, 60.38: H, 8.11; N. 7.68%. Found C, 60.28; H, 8.28; N, 7.88%.

EXAMPLE 10

1-(2-Methoxyphenyl)-4-[2-(cyclohexylthio)-2-(2-pyridinyl)ethyl]piperazine

The title compound was prepared following the procedure of Example 5 using cyclohexyl disulphide as a reactant in place of isopropyl disulphide. The product was obtained as the hydrochloride, m.p. 91°–92° C.

$C_{24}H_{33}N_3OS.3HCl.1.25H_2O$ requires: C, 53.04; H, 7.14; N, 7.73%. Found C, 53.08; H, 7.29; N, 7.61%.

EXAMPLE 11

1-(2-Methoxyphenyl)-4-[3-(cyclopentylthio)-3-(2-pyridinyl)propyl]piperazine

The title compound was prepared following the procedure of Example 6 using cyclopentyl disulphide as reactant in place of cyclohexyl disulphide. The product was obtained as the hydrochloride, m.p. 95°–97° C.

$C_{24}H_{33}N_3OS.2HCl.1.5H_2O$ requires: C, 56.35; H, 7.49; N, 8.21%. Found C, 56.17; H, 7.60; N, 8.12%.

EXAMPLE 12

1-(2-Methoxyphenyl)-4-[3-(cyclopentylsulphonyl)-3-(2-pyridinyl)propyl]piperazine The title compound was prepared following the procedure of Example 8 using 1-(2-methoxyphenyl)-4-[3-(cyclopentylthio)-3-(2-pyridinyl)propyl]piperazine as the starting material. The product was obtained as the hydrochloride, m.p. 145°–146° C.

$C_{24}H_{33}N_3O_3S.2HCl.2H_2O$ requires: C, 52.17; H. 7.11; N. 7.60%. Found C, 52.25: H, 7.01; N, 7.71%.

EXAMPLE 13

1-(2-Methoxyphenyl)-4-[2-(cyclohexylsulphonyl)-2-(2-pyridinyl)ethyl]piperazine The title compound was prepared following the procedure of Example 8 using 1-(2-methoxyphenyl)-4-[2-(cyclohexylthio)-2-(2-pyridinyl)ethyl]piperazine as the starting material. The product was obtained as the hydrochloride, m.p. 75°–76° C.

$C_{24}H_{33}N_3O_3S.3HCl.2H_2O$ requires: C, 50.48; H, 6.71; N, 7.36%. Found C, 50.48; H, 6.80; N, 7.14%.

EXAMPLE 14

1-(2-Methoxyphenyl)-4-[3-(cyclohexyl)-3-(2-pyridinyl)propyl]piperazine

To a dry toluene (14 ml) solution of 1-(2-methoxyphenyl)-4-(3-pyridinylpropyl)piperazine (1.5 g, 4.82 mmol) under argon at 0° C. was added nBuLi (7.4 ml, 1.3M). After anion formation the solution was treated with cyclohexylbromide (1.18 ml, 9.64 mmol) in toluene (2.8 ml). The reaction mixture was allowed to attain room temperature and stirred overnight. The reaction mixture was treated with HCl (1N) and the organic layer discarded. The acid layer was washed with ether, taken to pH 13 with solid NaOH (cool) and extracted with chloroform.

The organic layer was washed with sat NaCl solution, dried ($MgSO_4$) filtered and reduced to an oil.

The product was eluted from a silica gel pressure column with ethyl acetate and convened to the hydrochloride salt, m.p. 140°–142° C.

$C_{25}H_{35}N_3O.3HCl.1.25H_2O$ requires: C, 57.14; H. 7.77: N. 8.00%. Found C. 57.27; H, 7.82; N, 7.94%.

EXAMPLE 15

1-(2-Methoxyphenyl)-4-[3-butan-(2-pyridinyl-4-dicyclohexyl-4-ol]piperazine

To a solution of 1-(2-methoxyphenyl)4-(3-pyridinylpropyl)piperazine (3.0 g, 9.24 mmol) in anhydrous toluene (30 ml) was added, under argon with stirring at 0° C., nBuLi (7.8 ml, 1.3M). After twenty minutes di(cyclohexane) ketone (2.36 ml, 12 mmol) was added and the reaction stirred at room temperature for 13 hours.

1N HCl was added and a grey precipitate removed by filteration. The aqueous layer was washed with dichloromethane, taken to pH 13 by the addition of solid sodium hydroxide (with cooling). The organic material was extracted into ethylacetate, washed with brine, dried (MgSO$_4$), filtered and reduced to an oil.

The residue was purified by pressure silica gel column chromatography to give the title compound which was convened to the HCl salt, m.p. 175°–176° C., with ethereal HCl.

$C_{32}H_{47}N_3O_2 \cdot 3HCl \cdot 1.5H_2O$ requires: C, 59.85; H, 8.32; N, 6.54%. Found C, 60.02; H, 8.34; N, 6.53%.

We claim:

1. A compound of general formula

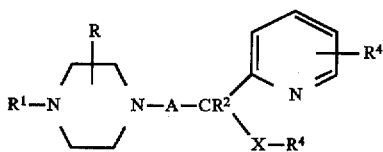

or a pharmaceutically acceptable acid addition salt thereof wherein

R represents hydrogen or one or two same or different $C_1$–$C_6$ alkyl groups $R^1$ is mono or bicyclic aryl selected from phenyl, naphthyl and bezodioxan-5-yl, each optionally substituted by one or more substituents selected from $C_{1-6}$alkyl, $C_{1-6}$alkoxy, halogen, halo($C_{1-6}$)alkyl, nitro, nitrile, ($C_{1-6}$) alkoxycarbonyl, amino, mono($C_{1-6}$)alkylamino and di($C_{1-6}$)alkylamino, or $R^1$ is mono or bicyclic heteroaryl selected from pyrimidinyl, quinolinyl, isoquinolinyl, and indolyl, each optionally substituted by one or more substituents selected from $C_{1-6}$alkyl, $C_{1-6}$ alkoxy, halogen, halo($C_{1-6}$)alkyl, nitro, nitrile, ($C_{1-6}$)alkoxycarbonyl, amino, mono($C_{1-6}$)alkylamino and di($C_{1-6}$)alkylamino $R^2$ is hydrogen or $C_1$–$C_6$ alkyl $R^3$ is hydrogen or cycloalkyl $R^4$ is hydrogen or $C_1$–$C_6$ alkyl A is an alkylene chain of 1 to 3 carbon atoms optionally substituted by one or more lower alkyl groups and X is —CO—, —CR$^5$OH— (where R$^5$ is hydrogen, $C_1$–$C_6$ alkyl or cycloalkyl), S, SO or SO$_2$ or X can also be —(CH$_2$)$_n$— (where n is 0, 1 or 2) when $R^3$ is cycloalkyl.

2. A compound as claimed in claim 1 in which $R^1$ is monocyclic aryl or bicyclic heteroaryl.

3. A compound as claimed in claim 1 in which $R^3$ is cyclohexyl.

4. A compound as claimed in claim 1 in which X is —CO—. —CHOH—, —S—, —SO$_2$— or —CH$_2$—.

5. A compound as claimed in claim 1 which is

R *, R*-1-(2-methoxyphenyl)-4-[(2-propan-(2-pyridinyl)-3-cyclohexyl)-3 -ol]piperazine, R*, S*-1-(2-methoxyphenyl)4-[(2-propan-(2-pyridinyl)-3-cyclohexyl)-3-ol]piperazine, R*, R*-1-(2-methoxyphenyl)4-[3-butan-(2-pyridinyl)4-cyclohexyl)4-ol]piperazine, R*, S*-1-(2-methoxyphenyl)4-[3-butan-(2-pyridinyl)4-cyclohexyl)-4-ol]piperazine, 1-(2-methoxyphenyl-4-[3-(2-pyridinyl)4-cyclohexyl4-one]piperazine, 1-(2-methoxyphenyl)-4-[4-(cyclohexyl)-3-(2-pyridinyl) butyl]piperazine, 1-(2-methoxyphenyl)-4-[1-(( 1-methyl)thioethyl)-1-(2-pyridinyl)ethyl]piperazine, 1-(2-methoxyphenyl)-4-[3-(cyclohexylthio)-3-(2-pyridinyl)propyl]piperazine, 1-(2-methoxyphenyl)-4-[3-(cyclohexylsulphoxy)-3-(2-pyridinyl)propyl]piperazine, 1-(2-methoxyphenyl)-4-[3-(cyclohexylsulphonyl)-3-(2-pyridinyl)propyl]piperazine, 1-(2-methoxyphenyl)-4-[5-(cyclohexyl)-3-(2-pyridinyl) pentyl]piperazine, 1-(2-methoxyphenyl)-4-[2-(cyclohexylthio)-2-(2-pyridinyl)ethyl]piperazine, 1-(2-methoxyphenyl)-4-[3-(cyclopentylthio)-3-(2-pyridinyl)propyl]piperazine, 1-(2-methoxyphenyl)-4-[3-(cyclopentylsulphonyl)-3-(2-pyridinyl)propyl]piperazine, 1-(2-methoxyphenyl)-4-[2-(cyclohexylsulphonyl)-2-(2-pyridinyl)ethyl]piperazine, 1-(2-methoxyphenyl)-4-[3-(cyclohexyl)-3-(2-pyridinyl) propyl]piperazine or 1-(2-methoxyphenyl)-4-[3-butan-(2-pyridinyl)-4-dicyclohexyl-4-ol]piperazine or a pharmaceutically acceptable acid addition salt thereof.

6. A pharmaceutical composition for use as a 5HT$_{1A}$ antagonist comprising a compound claimed in claim 1 in association with a pharmaceutically acceptable carrier.

* * * * *